(12) United States Patent
Wiget (10) Patent No.: US 9,011,767 B2
(45) Date of Patent: Apr. 21, 2015

(54) TRANSPORTABLE VACUUM ASSISTED DECONTAMINATION UNIT AND DECONTAMINATION PROCESS

(71) Applicant: STERIS Inc., Temecula, CA (US)

(72) Inventor: Paul A. Wiget, Mentor, OH (US)

(73) Assignee: STERIS Inc., Temecula, CA (US)

( * ) Notice: Subject to any disclaimer, the term of this patent is extended or adjusted under 35 U.S.C. 154(b) by 0 days.

(21) Appl. No.: 14/230,474

(22) Filed: Mar. 31, 2014

(65) Prior Publication Data

US 2014/0294670 A1   Oct. 2, 2014

Related U.S. Application Data (60) Provisional application No. 61/806,989, filed on Apr. 1, 2013.

(51) Int. Cl.
*A61L 2/20* (2006.01)
*E04H 1/12* (2006.01)
*A61L 2/26* (2006.01)

(52) U.S. Cl.
CPC ............... *A61L 2/20* (2013.01); *E04H 1/1277* (2013.01); *A61L 2/208* (2013.01); *A61L 2/26* (2013.01); *A61L 2202/13* (2013.01); *A61L 2202/16* (2013.01)

(58) Field of Classification Search
CPC .................................. A61L 2/20; A61L 2/26

USPC ............ 422/28, 29, 33, 292, 295, 298; 588/1, 588/299, 401
See application file for complete search history.

(56) References Cited

U.S. PATENT DOCUMENTS

| | | | |
|---|---|---|---|
| 5,074,897 A | 12/1991 | Sikich | |
| 7,993,601 B2 | 8/2011 | Weiss et al. | |
| 8,128,888 B2 | 3/2012 | Bacik et al. | |
| 8,153,078 B2 | 4/2012 | Bacik et al. | |
| 8,163,236 B1 | 4/2012 | Bacik et al. | |
| 8,182,743 B1 | 5/2012 | Bacik et al. | |
| 8,216,523 B2 | 7/2012 | Meilander et al. | |
| 2008/0267819 A1* | 10/2008 | Bacik et al. ..................... | 422/29 |
| 2012/0233923 A1 | 9/2012 | Diercks | |

FOREIGN PATENT DOCUMENTS

DE   10 2011 014 104 B3   6/2012
WO   2008/109252 A1   9/2008

OTHER PUBLICATIONS

International Search Report and the Written Opinion for corresponding International Application No. PCT/US2014/032334 mailed Jul. 10, 2014.

* cited by examiner

*Primary Examiner* — Sean E Conley
(74) *Attorney, Agent, or Firm* — Renner, Otto, Boisselle & Sklar, LLP (57) ABSTRACT

The disclosed invention relates to a portable, vacuum assisted decontamination unit. The invention also relates to a vacuum assisted decontamination process. The decontamination unit may be ruggedized for use in hostile environments such as those that may be anticipated for military applications.

18 Claims, 4 Drawing Sheets

TRANSPORTABLE VACUUM ASSISTED DECONTAMINATION UNIT AND DECONTAMINATION PROCESS

TECHNICAL FIELD

This invention relates to a transportable, vacuum assisted decontamination unit and to a decontamination process.

BACKGROUND

Decontaminant generating systems, such as those used to generate vaporous hydrogen peroxide (VHP), have been used to decontaminate large enclosures such as aircrafts from contaminants such as bacteria, molds, fungi, yeasts, and the like. In military applications, it may be necessary to use decontaminant systems in defense against chemical and biological weapons.

SUMMARY

Military pilots are provided with an ensemble of specialized protective equipment that enables the pilot to operate the aircraft in the presence of chemical and biological contamination. After a chemical or biological incident, the aircraft is decontaminated to permit operation without the need for such protective equipment. After the chemical or biological incident, the pilot's protective ensemble must be replaced. Since the pilot flight equipment (PFE) and personal protective equipment (PPE) are highly specialized, and in some cases custom made or customized for the individual pilot, disposal of the ensemble represents a significant expense and significant challenge if pilots in forward positions require a complete resupply of this equipment.

It would be advantageous for the military to use readily transportable decontaminant systems in the field in defense against chemical and biological weapons. This invention relates to a decontamination unit that is self-contained, readily transportable and is ruggedized for use in hostile environments.

In one aspect of the invention, there is provided a transportable vacuum assisted decontamination unit that includes: a housing containing a decontamination chamber and a decontaminant processing section; and a military master pallet on which the housing is positioned; the decontamination chamber including at least one gas inlet for admitting a gaseous decontaminant into the decontaminant chamber from the decontaminant processing section and at least one gas outlet for evacuating the decontamination chamber; the decontaminate processing section including a decontaminant generator and vacuum means; the decontaminant generator being adapted for generating a gaseous decontaminant and the vacuum means adapted for generating negative pressure within the decontamination chamber for drawing the gaseous decontaminant into the decontamination chamber and for evacuating residual decontamination gases from the decontamination chamber, wherein the decontamination unit is ruggedized.

In one embodiment, the decontamination unit is self-contained with processing section further including a power generator, the power generator being adapted for providing electrical operating power for the decontaminant generator and the vacuum means. The power generator may be an internal combustion engine and an electric generator. In one embodiment, the internal combustion engine and the electric generator are combined in a single piece of equipment.

In one embodiment, the decontaminant generator includes a vaporizer, liquid decontaminant container and alkaline gas container.

In one embodiment, the decontamination processing section further includes a catalytic converter and filter.

The decontamination unit may be ruggedized such that the housing and the decontamination chamber are (1) hardened to ensure that five exposures to chemical, biological, radiological or nuclear contaminants, decontaminants and decontaminating procedures over a thirty-day period do not cause the housing or decontamination chamber to require corrective maintenance during that thirty-day period; (2) constructed to withstand temperatures ranging from about −32° C. to about 49° C.; (3) constructed to withstand relative humidities ranging from about 5% to about 100%; and (4) constructed to operate when exposed to conventional hazards of solar radiation, rain, fungus, salt fog, sand, dust, vibration and shock.

In another aspect of the invention, there is provided a process for operating the transportable vacuum assisted decontamination, the process including the steps of: placing one or more contaminated articles in the decontamination chamber; drawing a vacuum on the decontamination chamber and the contaminated articles therein; bringing the gaseous decontaminant from the decontaminant processing section into the decontamination chamber; contacting the contaminated articles in the decontamination chamber with the gaseous decontaminant for a pre-determined period of time to decontaminate the contaminated articles; drawing a vacuum on the decontamination chamber to evacuate residual gaseous decontaminant from the decontamination chamber and to aerate the decontamination chamber and the decontaminated articles contained therein; and removing the decontaminated articles from the decontamination chamber.

In one embodiment, the decontamination processing section includes a power generator and the process further includes operating the power generator to provide power to operate the decontaminant generator and the vacuum means.

In one embodiment, the decontaminant comprises a peracid, peroxide, hypochlorite, ozone, or a mixture of two or more thereof.

In one embodiment, the decontaminant comprises hydrogen peroxide. The decontaminant may further include an alkaline gas.

In one embodiment, the evacuated residual gaseous decontaminant includes hydrogen peroxide, and the process further includes converting the residual hydrogen peroxide to water vapor and oxygen.

BRIEF DESCRIPTION OF THE DRAWINGS

In the annexed drawings all parts and features have like references. The annexed drawings are schematic illustrations which are not necessarily proportioned accurately or drawn to scale.

DETAILED DESCRIPTION

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

The term "line" when referring to the drawings may refer to any conduit for conveying a fluid. The conduit may be in any desired form, for example, one or more pipes, tubings, channels, and the like. These may be made of materials sufficient to provide the required properties of strength, flexibility, and resistance to the fluids being conveyed. The lines may be ruggedized to permit use in hostile environments such as those that may be encountered in military applications.

The term "fluid" may refer to a liquid, gas, or mixture thereof.

The inventive decontamination unit, in its illustrated embodiment, will be described with reference to FIGS. 1-3.

In military applications, decontamination of pilot flight equipment (PFE) and personal protective equipment (PPE) is very challenging because of the range of fabrics and materials employed, and in many cases, the sensitive electronics that are incorporated into the helmets and other components used.

Figure 4:
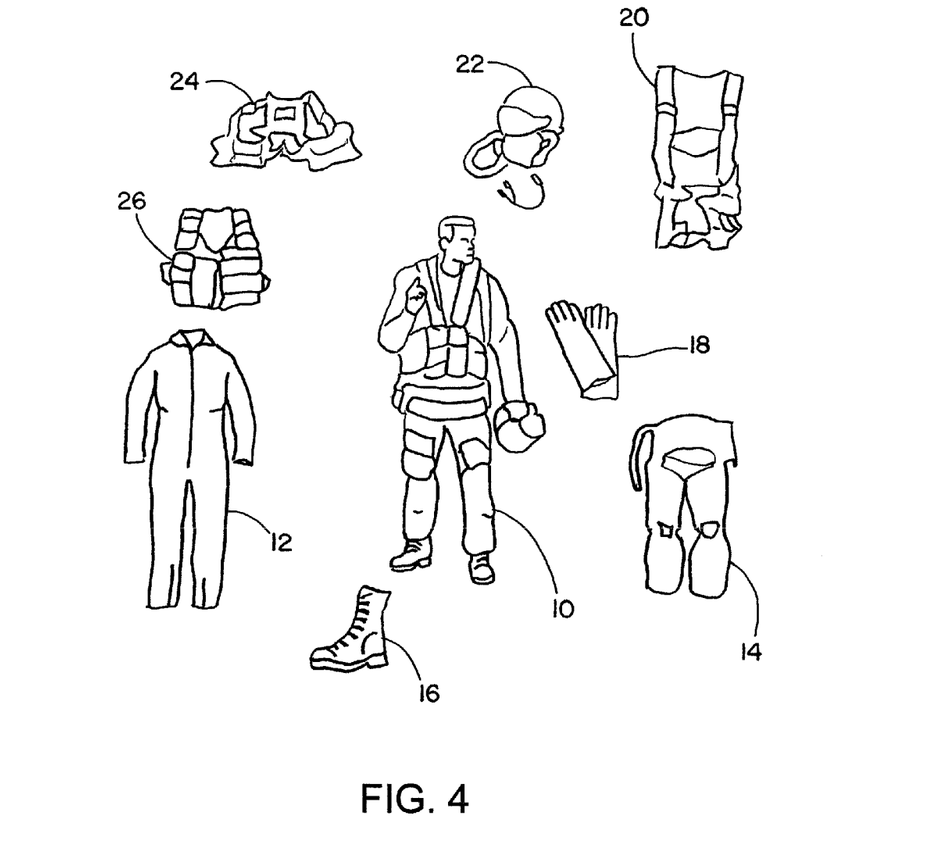
FIG. 4 is an illustration of pilot flight equipment on which the decontamination system of the present invention can be employed.

As illustrated in FIG. 4, the PFE of a military pilot 10 may include a flight suit 12, a G-suit 14, boots 16, gloves 18, harness 20, helmet 22, life preserver 24 and survival vest 26. Helmet 22 typically includes electronic and optical devices.

By using a vacuum assisted vaporized hydrogen peroxide (VHP) decontamination system, PFE/PPE and other sensitive equipment can be effectively and efficiently decontaminated. By reducing the pressure at which the decontaminant is employed, the rate of diffusion is greatly increased, allowing the decontaminant to penetrate rapidly throughout the garments and electronics. Another advantage of the low pressure is increased activity of the decontaminant. By removing a significant portion of the air from the enclosure during decontamination, the rate of interaction between the decontaminant and the contaminants of the PFE/PPE is increased.

Because the low pressure increases the activity of the decontaminant and the rate at which the decontaminant penetrates the PFE/PPE, lower concentrations of decontaminant can be employed, for shorter exposure times. This reduces the potential for adverse effects on materials (i.e., improved material compatibility) and also reduces the total time required for the decontamination, thus allowing the pilots to return to active duty more rapidly.

Figure 1:
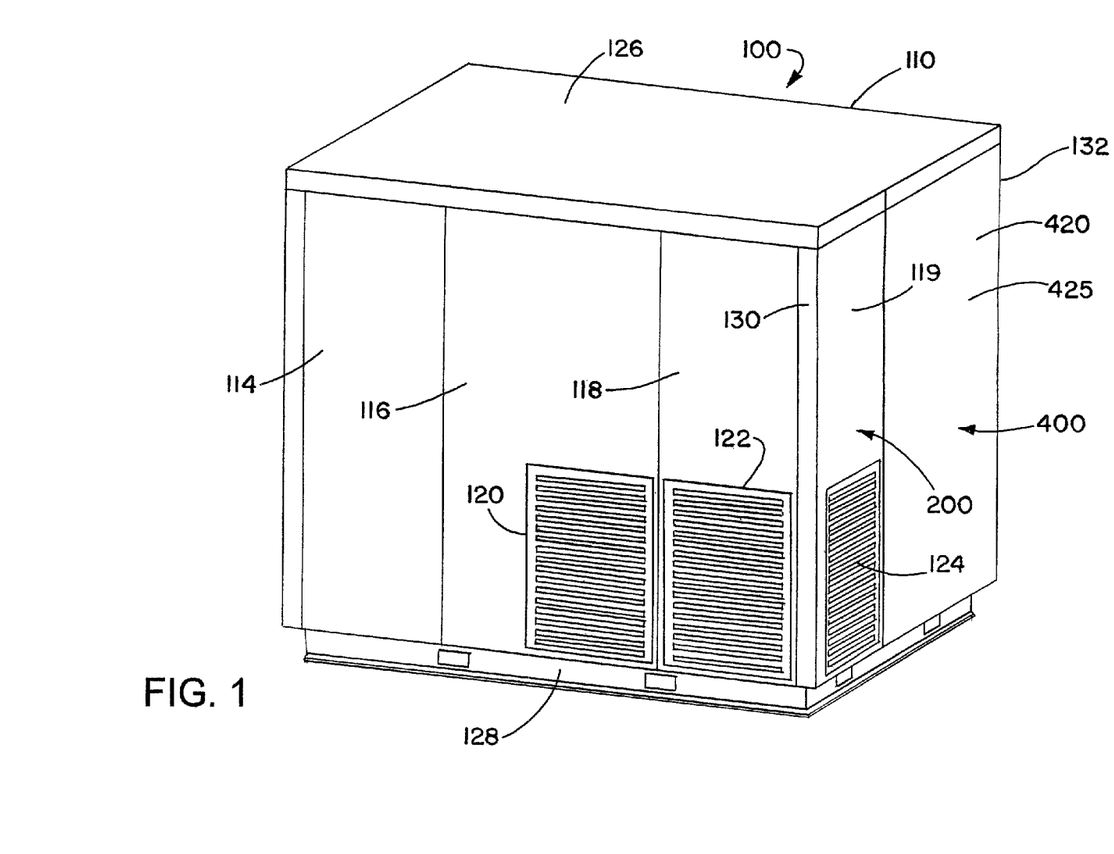
FIG. 1 is a schematic illustration of a decontamination unit within the scope of the present invention. The decontamination unit includes a decontaminant processing section and a decontamination chamber.

Referring to FIG. 1, exemplary decontamination unit 100 includes housing 110 which contains decontaminant processing section 200 and decontamination chamber 400. The housing 110 may include removable side panels 114, 116 and 118, side panel 119, and vents 120, 122 and 124. The housing 110 may also include top panel 126. The decontamination unit 100 is positioned on pallet 128. Part of the housing 110 forms the exterior walls of the decontamination chamber 400.

The decontamination unit 100 may be of sufficient size and weight to provide the decontamination chamber 400 with the desired internal volume to provide for decontamination on a large scale and yet allow the decontamination unit 100 to be readily transportable. The decontamination chamber 400 may have an internal volume in the range from about 0.5 to about 10 cubic meters, and in one embodiment from about 2.5 to about 7.5 cubic meters, and in one embodiment from about 4 to about 7 cubic meters, and in one embodiment from about 6 to about 7 cubic meters, and in one embodiment about 6.8 cubic meters. The decontamination unit 100 may have a height (as measured from the base support 128 to the top panel 126) in the range from about 0.5 to about 2.5 meters, and in one embodiment in the range from about 1 to about 2.5 meters, and in one embodiment in the range from about 1.5 to about 2.5 meters, and in one embodiment in the range from about 2 to about 2.5 meters, and in one embodiment in the range from about 2.3 to about 2.5 meters, and in one embodiment about 2.4 meters. The decontamination unit 100 may have a width (as measured from side 130 to side 132) in the range from about 1 to about 2.5 meters, and in one embodiment in the range from about 1.5 to about 2.5 meters, and in one embodiment in the range from about 2 to about 2.5 meters, and in one embodiment about 2.2 meters. The decontamination unit 100 may have a length in the range from about 1.2 to about 2.8 meters, and in one embodiment in the range from about 2 to about 2.8 meters, and in one embodiment in the range from about 2.5 to about 2.8 meters, and in one embodiment about 2.7 meters. The overall weight of the decontamination unit 100 may be in the range from about 500 to about 10,000 pounds (227 to 4536 Kg), and in one embodiment in the range from about 500 to about 7,500 pounds (227 to 3402 Kg), and in one embodiment in the range from about 1000 to about 7500 pounds (454 to 3402 Kg), and in one embodiment about 5000 pounds (2268 Kg). The decontamination unit 100 may be readily transported using conventional techniques, for example, the decontamination unit 100 may be transported using an airplane, ship, truck, and the like. The decontamination unit is positioned on and may be transported using pallet 128. Pallet 128 may be a standard military 463L master pallet.

The 463L master pallet is used for air transport by the United States Air Force. Cargo aircraft used by the United States Air Force may be configured to accept these pallets. The 463L master pallet is also used for combat offloads and aerial delivery or airdrop. The 463L master pallet is 88 inches (224 cm) wide, 108 inches (274 cm) long, and 2.25 inches (5.7 cm) high. The usable space is 84 inches (213 cm) by 104 inches (264 cm). The 463L master pallet may hold up to 10,000 pounds (4500 Kg) of cargo. The empty weight is 290 pounds (130 Kg). The 463L master pallet has a balsa wood core which is surrounded by a thin aluminum skin. There are 22 rings surrounding the edge, each rated at 7,500 pounds (3400 Kg).

The decontamination unit 100 may be used in hostile environments such as those that may be anticipated for military applications. When intended for use in such hostile environments the housing 110 as well as the decontamination chamber 400 may be ruggedized. Ruggedization may include resistance to anticipated operating conditions and hazards, including hot and cold temperatures, exposure to solar radiation, rain, fungus, salt fog, sand, dust, vibration and/or shock, as well as exposure to CBRN contaminants. The decontamination chamber 400 may be constructed of materials capable of withstanding exposure to decontaminants that may be used in the decontamination chamber 400 as well as the contaminants likely to be encountered. The decontamination chamber 400 may be insulated. The housing 110 and the decontamination chamber 400 may be constructed using any material that is sufficient to provide the apparatus with the desired properties of strength and yet be sufficiently lightweight to be transportable as well as being ruggedized. The materials of construction may include stainless steel, coated steel, aluminum, aluminum alloy, anodized aluminum, and the like. Various metal alloys may be used, including the stainless steel alloys SS304 and SS316, and aluminum alloy 6061. Non-reactive materials, such as polyethylene, polyvinyl chloride, fluorinated polymers such as polytetrafluoroethylene, and the like, may be used.

Figure 2:
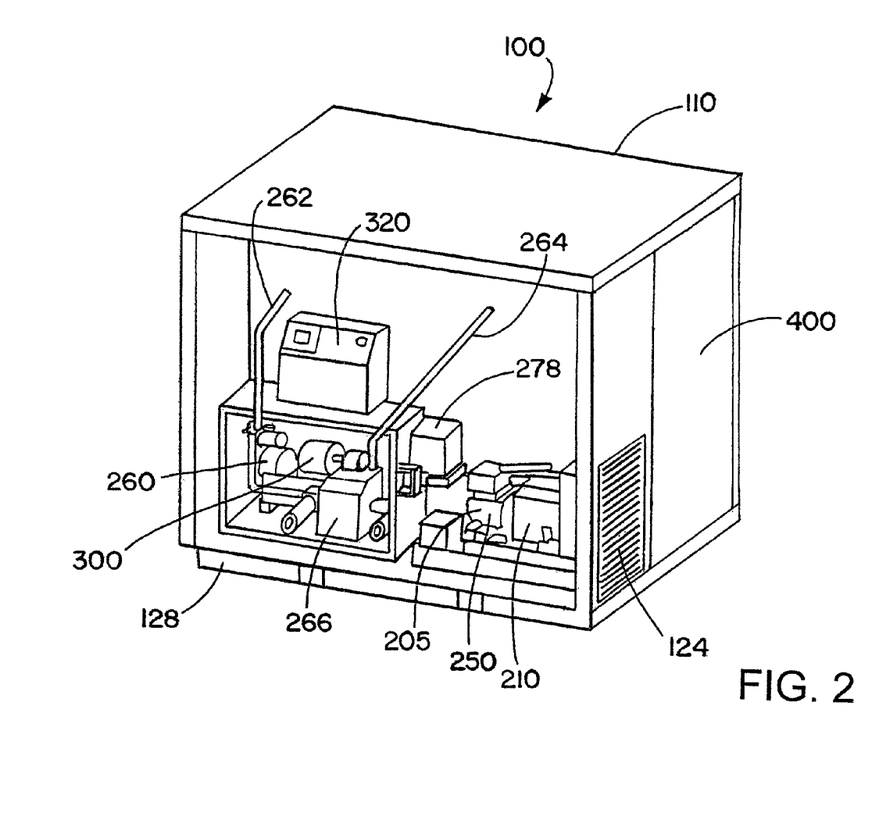
FIG. 2 is a schematic illustration of the decontamination unit of FIG. 1 with the sides of the unit removed to show the interior of the decontamination processing section.

Referring to FIG. 2, the decontaminant processing section 200 may include power generator 205, decontaminant generator 260 and vacuum pump 300. The power generator 205 may include internal combustion engine 210 and electric generator 250. Alternatively, the power generator may comprise a fuel cell. In one embodiment, the decontamination unit 100 may be regarded as being self-contained due to the fact that all of the power required to operate the decontaminant generator 260 may be provided by the power generator.

The power generator 205 may comprise internal combustion engine 210 in combination with electric generator 250 as shown in FIG. 2. The internal combustion engine 210 may comprise any internal combustion engine that is suitable for providing sufficient power to operate the electric generator 250. The internal combustion engine 210 may be operated using diesel fuel, gasoline, petroleum gas, propane gas, natural gas, liquefied petroleum gas, hydrogen gas, biofuels (e.g., ethanol, biodiesel fuel, etc.), and the like. The internal combustion engine 210 may comprise a spark ignition engine or a compression ignition engine. The internal combustion engine 210 may comprise a two-cycle engine, four-cycle engine, rotary engine, or gas turbine engine.

The electric generator 250 may comprise any electric generator that can be powered by the internal combustion engine 210 and provide sufficient power to operate the decontaminant generator 260, as well as any other electrically powered equipment used with the decontamination unit 100 including lighting, vacuum pumps, computers, monitors, controllers, recorders, and the like. The electric generator 250 may have a power rating in the range from about 4 to about 30 kVA, and in one embodiment in the range from about 4 to about 20 kVA, and in one embodiment in the range from about 4 to about 10 kVA.

The power generator 205 may comprise the internal combustion engine 210 and the electric generator 250 combined as a single piece of equipment. The power generator 205 may be ruggedized to permit use in hostile environments such as those that may be anticipated for military applications. The power generator may be sufficiently small and lightweight to allow the decontamination unit 100 to be transportable.

An example of a power generator that may be used is available from Northern Lights under the trade designation NL673L2. This power generator employs a Lugger L844 engine which is a vertical, three cylinder diesel engine. The Lugger L844 engine is a four cycle, liquid cooled, naturally aspirated, overhead valve, industrial-duty, diesel engine. This engine may operate at 1500 RPM or 1800 RPM. The AC output of the electric generator may be 6 kW or 5 kW. The specifications and dimensions for this power generator may be as follows:

| AC Output | |
|---|---|
| 6 kW | 60 Hz, 1800 RPM, 1 Ph, 1.0 PF, 120-240 V/25A, 120 V/50 A |
| 5 kW | 50 Hz, 1500 RPM, 1 Ph, 1.0 PF, 220 V/22.7 A |
| Engine | |
| Displacement | 46.4 in$^3$ (0.76 ltr) |
| Bore/Stroke | 2.64/2.83 in (67/72 mm) |
| HP @ RPM | 9.9/1800 7.7/1500 |
| Approx. Fuel Use | |
| 1800 RPM @ full load | 0.59 gph (2.2 lph) |
| 1800 RPM @ full load | 0.32 gph (1.2 lph) |
| 1500 RPM @ full load | 0.50 gph (1.9 lph) |
| 1500 RPM @ full load | 0.28 gph (1.1 lph) |

The NL 673L2 power generator may have a base length of 32.8 inches (83.4 cm), a base width of 15.3 inches (39.40 cm), a height of 27 inches (68.6 cm), and a dry weight of 377 pounds (171 kg).

As an alternative to the internal combustion engine 210 and electric generator 250, the power generator may comprise a fuel cell. The fuel cell may be regarded as an electrochemical energy conversion device. It produces electricity from various external quantities of fuel (on an anode side) and oxidant (on a cathode side). These react in the presence of an electrolyte. Generally, the reactants flow in and reaction products flow out while the electrolyte remains in the cell. Various combinations of fuel and oxidant may be used. The fuel cell may comprise a hydrogen cell which uses hydrogen as the fuel and oxygen as the oxidant. Other fuels may include hydrocarbons and alcohols. Other oxidants may include air, chlorine and chlorine dioxide. The fuel cell may work by catalysis, separating the component electrons and protons of the reactant fuel, and forcing the electrons to travel through a circuit, hence converting them to electrical power. The catalyst may comprise a platinum group metal or alloy. Another catalytic process takes the electrons back in, combining them with the protons and the oxidant to form waste products (typically water and carbon dioxide).

The decontamination chamber 400 may be a single door chamber. Alternatively, the decontamination chamber 400 may be a double door chamber having a first entrance 420 with a first door 425, and an opposite second entrance with a second door (not shown). The first entrance 420 may be referred to as the "contaminated" side of the decontamination chamber and the second entrance may be referred to as the "clean" side of the decontamination chamber.

In operation of the decontamination unit, the chamber 400 is closed, and air is removed from the chamber 400 to lower the pressure to a target pressure. The pressure being selected to match the pressure limits the loaded equipment can handle. For example, much of the equipment used on aircraft, and issued to pilots, has a requirement to survive exposure to pressures at altitudes up to 40,000 feet (this is approximately 140 mmHG, or 2.7 psia). For equipment used on aircraft like the U2, the altitude will be much greater (i.e. pressure much lower). Other items, such as clothing, or non-electronic hardware including firearms may be able to survive exposure to complete vacuum.

Once at the target pressure, the decontaminant is dispensed into the chamber. In the case of hydrogen peroxide, this would involve injecting hydrogen peroxide solution into a vaporizer, and allowing the generated gasses to enter the chamber.

Depending on the concentration desired, either a single dose, or multiple doses of liquid hydrogen peroxide would be injected. A similar vaporizer arrangement could be used for other liquid components of the decontaminant. For gaseous components of the decontaminant the component could be injected into the chamber, and the increase in pressure monitored to determine when an appropriate amount has been added.

Once conditions are met, the system would maintain those conditions for a set period of time, after which the chamber would be re-evacuated and either additional pulses of decontaminant are added to obtain the desired contact time, or the chamber is aerated to allow the equipment to be removed and returned to use.

The decontaminant may comprise one or more oxidants such as peracids (e.g., peracetic acid) and/or peroxides (e.g., hydrogen peroxide), and the like. Oxidants such as hypochlorites, ozone, and the like, may be used. Mixtures of two or more of these may be used. Aqueous solutions of these oxidants may be used. The decontaminant may be combined with a solvent. The solvent may be miscible with water. When the decontaminant comprises hydrogen peroxide, the solvent may be used to enhance the solubility of the hydrogen peroxide and its associated decomposition products in the contaminant and thereby enhance the rate of destruction of the contaminant. The solvent may comprise a mixture of water and tert-butyl alcohol; water and acetonitrile; or water, acetronitrile and isopropyl alcohol. Other suitable solvents may include tetrahydrofuran, dimethylsulfoxide, acetone, acetaldehyde, propylene oxide, acetamide, diethylamine, dimethoxyethane, or a mixture of two or more thereof. The solvent concentration in the combined mixture of decontaminant and solvent may be in the range up to about 60% by weight solvent, and in one embodiment in the range from about 20 to about 60% by weight solvent. The decontaminant may be combined with an alkaline gas such as ammonia in applications wherein an increase in the pH of the decontaminant may be desired.

Vaporous hydrogen peroxide (VHP), which may be generated from an aqueous solution of hydrogen peroxide, may be used as the decontaminant. The aqueous solution may comprise from about 30% to about 40% by weight hydrogen peroxide, and in one embodiment about 35% by weight hydrogen peroxide; and from about 60% to about 70% by weight water, and in one embodiment about 65% by weight water. By adding an alkaline gas that is soluble in the hydrogen peroxide (ammonia, for example), the pH of the decontaminant may be controlled. The volumetric ratio of VHP to ammonia gas may be in the range from about 1:1 to about 1:0.0001.

VHP, when used in combination with ammonia gas, may be referred to as modified VHP or mVHP. VHP and/or mVHP may be effective microbial and chemical decontaminants because they may provide a broad spectrum of activity against a wide variety of pathogenic microorganisms and chemical pathogenic agents, such as hard to destroy spores of *Bacillus stearothermophilus, Bacillus anthracis*, smallpox virus, and the like. They may be also effective at or close to room temperature (e.g., about 15 to about 30° C.), making them suitable for use in the decontamination chamber 400 with little or no heating. VHP and/or mVHP may have good material compatibility, rendering them safe for use with a variety of equipment and materials, including electronic equipment, soft furnishings, brass and chrome fixtures, and the like. VHP may degrade to water and oxygen over time, which may not be harmful to a person subsequently entering the decontamination chamber 400. Low levels of hydrogen peroxide (for example, about 1 ppm, or less) that may remain in the decontamination chamber 400 after the decontamination process has been completed may not be considered to pose a risk to a person entering the chamber.

The decontamination process may be controlled using control unit 320. The decontamination chamber 400 may contain internal monitors for measuring decontaminant levels, temperature, internal gas flow, pressure, and the like. These monitors may be used in combination with controllers for adjusting decontaminant concentration levels, temperature, internal gas flow rates, pressure, and the like.

Figure 3:
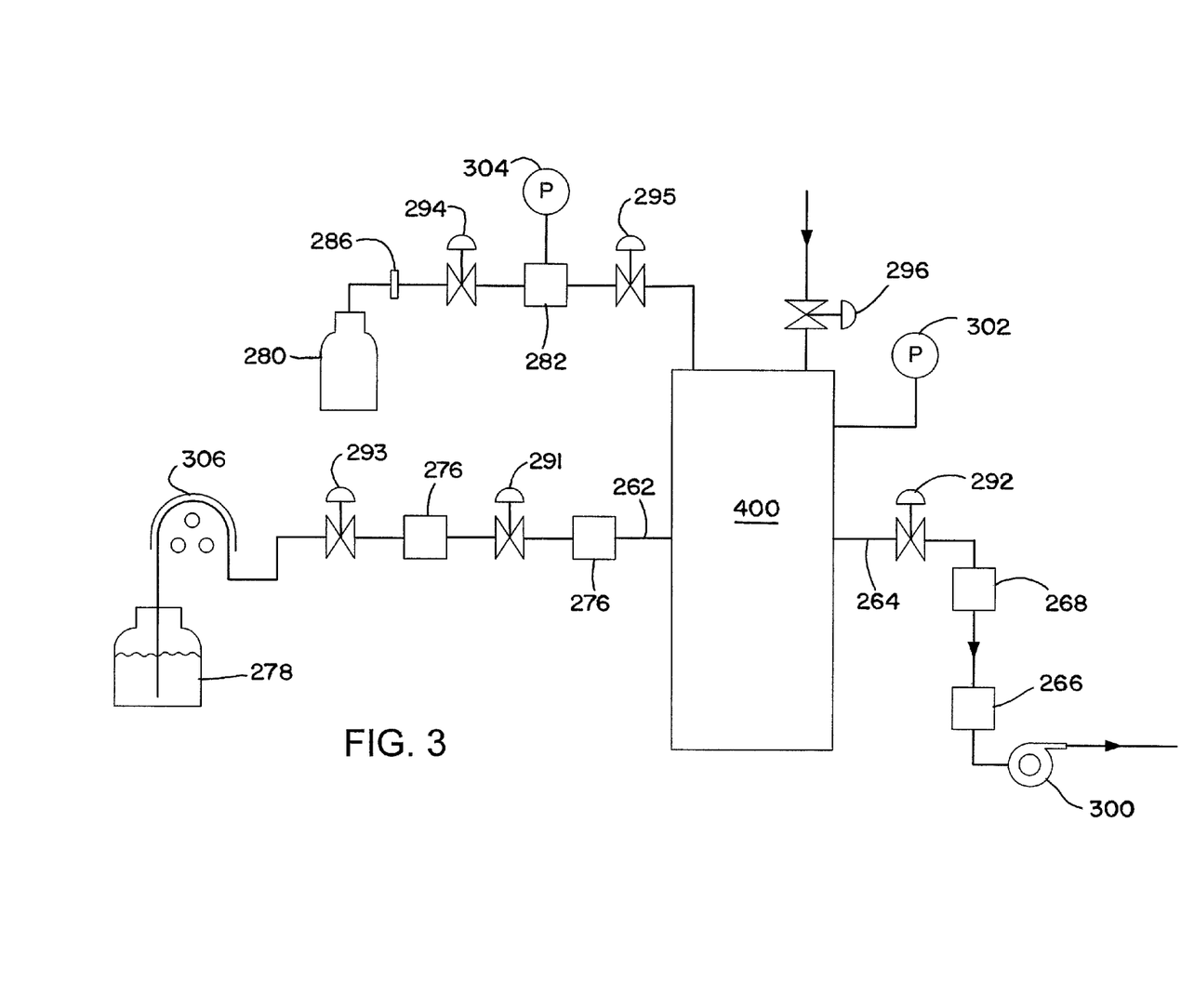
FIG. 3 is a flow sheet showing the operation of the decontaminant unit illustrated in FIGS. 1 and 2.

Referring to FIG. 3, operation of the decontamination unit, in one embodiment includes the following steps. The chamber 400 is loaded with the objects or materials to be decontaminated (i.e., "the load"). All of valves 291, 292, 293, 294, 295 and 296 are closed. The door 425 (or doors) of the chamber 400 is closed. The cycle is started by turning on vaporizer 276 so that it can pre-heat to desired set point (typically 110° C.). Valve 292 and valve 295 are opened, and the remaining valves are closed. Vacuum pump 300 is turned on, and the pressure within chamber 400 is allowed to drop to a specified level (pressure transducer 302 monitors the pressure). The final pressure is determined by limits on the equipment (or load) being processed. Different equipment is rated to different altitudes, so the final vacuum level will vary to match the rated altitude of the load.

Valves 292 and 295 are closed. Valve 293 is then opened and the dispensing pump 306 is run to transfer the desired amount of hydrogen peroxide solution (for example, 35% or 59%, or other) from the liquid hydrogen peroxide reservoir 278 into hydrogen peroxide accumulator 276. The amount of hydrogen peroxide will vary depending on a number of factors, including the size of chamber and the nature of the load. In one embodiment, the mass/volume of hydrogen peroxide will be selected to provide concentrations of hydrogen peroxide in the chamber of up to 5 mg/L, or more usually 1-2 mg/L, or for sensitive equipment 0.1-0.5 mg/L.

Valve 294, located between the alkali gas cylinder 280 and the alkali gas accumulator 282, is opened and the pressure in alkali gas accumulator 282 is monitored by pressure transducer 304. When the pressure in accumulator 282 reaches the set point, valve 294 is closed. The limiting orifice 286 serves to impede the flow of gas so that the pressure rise is sufficiently slow to allow the pressure transducer 304 to follow the pressure change and react when the set point is reached. The pressure of alkali gas in the accumulator 282 will be determined based on the volume of the chamber 400, the nature of the load, and intended final concentration of hydrogen peroxide. The molar ratio of alkali gas to hydrogen peroxide may be approximately 1:10; or in the range 1:100 to 1:10 alkali gas : hydrogen peroxide. For example, if the concentration of $H_2O_2$ is 1 mg/L, this is equivalent to 0.03 milliMoles/L, so the alkali gas concentration will be 0.003 mMoles/L.

When both accumulators (hydrogen peroxide 276 and alkali gas 282) are charged, valve 295 and valve 291 are opened. The low pressure in the chamber will draw the contents of the accumulators 276 and 282 into the chamber 400. The hydrogen peroxide solution will pass through the vaporizer 276 where contact with the heated surfaces, and the reduced absolute pressure will cause the liquid to boil. Upon entering the chamber 400 the decontaminant gases (alkali gas, and the newly boiled hydrogen peroxide) will diffuse rapidly (due to the low pressure the diffusion rates will be greatly accelerated compared with diffusion at atmospheric pressure) throughout the chamber, and interact with the load. Pressure in the chamber will be increased due to the addition of the decontaminant gases. In the embodiment illustrated in FIG. 3, the alkali gas and the $H_2O_2$ enter the chamber through two separate lines. In another embodiment, the decontaminant gasses enter the chamber in a single line.

After entry of the decontaminant gasses into the chamber, an experimentally determined dwell time is allowed to pass. This time is to allow the decontaminant gases to interact with the load, and to react with the contaminants on the load.

When the decontaminant gas enters into the decontamination chamber 400 and contacts the contaminated articles to be decontaminated, the process may be regarded as a dry process characterized by the absence of condensate formation on the surfaces of the contaminated articles being decontaminated. Alternatively, the process may be regarded as a wet process characterized by the formation of a condensate in the form of a liquid film on the surfaces of the contaminated articles. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide.

The progress of the decontamination process may be monitored using one or more decontamination or sterilization indicators. These indicators may contain a biological indicator. The biological indicator may comprise one or more test organisms which may be more resistant to the decontamination process than the organisms to be destroyed by the decontamination process. The test organism may be placed in contact with an incubation medium to determine whether the decontamination process was effective.

After the initial cycle is completed, the vacuum pump 300 is started, valves 295 and 293 are closed and valve 292 is opened, allowing the pressure to drop to the set point (see above), after which valve 292 is closed.

The steps of dispensing components, flooding the chamber and re-evacuating are repeated for a pre-determined number of pulses. The number of decontaminant pulses for each application will vary depending on the apparatus design, load size, load materials and degree of contamination.

After the prescribed number of decontaminant pulses, aeration of the chamber is conducted. During aeration, the vacuum system is used to rapidly remove decontamination gases from the decontamination chamber 400. This minimizes the overall sterilization cycle time and cost, and can improve efficiency. The reduced exposure time eliminates or reduces the potential material compatibility issues that may occur when load materials include, for example, polyurethane, nylon 6/6, or cast acrylic. Such materials have been shown to be absorptive of hydrogen peroxide when exposed for longer periods of time.

For each aeration pulse, valve 292 is opened and vacuum pump 300 is run to a set point pressure. Valve 292 is then closed and valve 296 is opened, allowing air to enter the chamber 400 and return to atmospheric pressure (or some pressure below atmospheric, but elevated compared to decontamination cycle). This allows air to enter, diluting the residual decontaminant gasses.

Valve 296 is then closed and valve 292 is opened to lower the pressure to a set point. This removes air and the residual decontaminant gasses. The aeration steps are repeated for a pre-determined number of pulses, or until concentration of decontaminant gases measured in chamber is reduced to pre-determined safe levels.

The spent gases are drawn out of the decontamination chamber through line 264 into filter 268 and to catalytic converter 266. The catalytic converter 266 may be used to destroy residual amounts of the decontaminant that may be in the gaseous air stream. For example, the catalytic converter 266 may be used to convert residual hydrogen peroxide to water vapor and oxygen. The catalyst may comprise any transition metal, transition metal oxide, or combination thereof, having the desired catalytic properties. The catalyst may include Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The filter 268 may comprise a carbon filter and a high efficiency particle air (HEPA) filter.

When the decontamination cycle is over, all valves are closed, the vacuum pump is stopped and the vaporizer heater(s) are turned off. The door(s) of the chamber are opened and the load is retrieved.

In one embodiment, the decontamination unit is not mounted on a military pallet, but is instead installed as a permanent or semi-permanent apparatus operated using standard external power. The decontamination unit includes: a housing containing a decontamination chamber and a decontaminant processing section. The decontamination chamber includes at least one gas inlet for admitting a decontaminant gas into the decontaminant chamber from the decontaminant processing section and at least one gas outlet for permitting the decontaminant gas to flow out of the decontamination chamber. The decontaminate processing section is adapted to be operated using standard external power, and includes a decontaminant generator, a catalytic converter and vacuum means, the vacuum means adapted for generating negative pressure within the decontamination chamber, the decontaminant generator being adapted for generating the decontamination gas and the catalytic converter adapted for destroying residual amounts of decontaminant upon completion of the decontamination process. The decontamination unit may be ruggedized.

The contaminated articles may be contaminated with any contaminant. The articles may comprise any article that may be stored in the decontamination chamber 400. These may include PFE/PPE, military weapons, clothing, and body armor, as well as sensitive equipment such as computers, test equipment, optical devices, electronic devices, communications equipment, and the like. The contaminant may comprise one or more chemical, biological, radiological and/or nuclear (CBRN) warfare agents.

Different levels of decontamination may be accomplished within the decontamination chamber 400. As used herein, the term "decontamination" is intended to encompass both microbial decontamination as well as chemical decontamination--the destruction of chemical agents, or their conversion to harmless or odorless compounds. Decontamination may also encompass the neutralizing of unpleasant odors, such as tobacco smoke, perfume, or body odor residues, and odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination encompasses sterilization, the highest level of biological contamination control, which connotes the destruction of all living microorganisms. The term also includes disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed in the decontamination process include bacterial spores, vegetative bacteria, viruses, molds, and fungi. Some of these may be capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl)sulfide (mustard gas or "HD") and dichloro(2-chlorovinyl)arsine (Lewisite); nerve agents, such as ethyl-N,N dimethyl phosphoramino cyanidate (Tabun or agent GA), o-ethyl-S-(2-diisopropyl aminoethyl)methyl phosphono-thiolate (agent VX), isopropyl methyl phosphonofluoridate (Sarin or Agent GB), methylphosphonofluoridic acid 1,2,2-trimethylpropyl ester (Soman or Agent GD).

The decontamination system described herein can be used as an added capability to other systems such as TCRWAD (tactical, cargo, rotary, wing aircraft decontamination) systems.

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A transportable vacuum assisted decontamination unit, comprising:
a housing containing a decontamination chamber and a decontaminant processing section; and
a military master pallet on which the housing is positioned;
the decontamination chamber comprising at least one gas inlet for admitting a gaseous decontaminant into the decontamination chamber from the decontaminant processing section and at least one gas outlet for evacuating the decontamination chamber;
the decontaminate processing section comprising a decontaminant generator and vacuum means; the decontaminant generator being adapted for generating a gaseous decontaminant and the vacuum means adapted for generating negative pressure within the decontamination chamber for drawing the gaseous decontaminant into the decontamination chamber and for evacuating residual decontamination gases from the decontamination chamber,
wherein the decontamination unit is ruggedized.

2. The decontamination unit of claim 1, wherein the decontamination processing section further comprises a power generator, the power generator being adapted for providing electrical operating power for the decontaminant generator and the vacuum means.

3. The decontamination unit of claim 2, wherein the power generator comprises an internal combustion engine and an electric generator.

4. The decontamination unit of claim 3, wherein the internal combustion engine and the electric generator are combined in a single piece of equipment.

5. The decontamination unit of claim 1, wherein the decontaminant generator comprises a vaporizer, liquid decontaminant container and alkaline gas container.

6. The decontamination unit of claim 1, wherein the decontamination processing section further comprises a catalytic converter and filter.

7. The decontamination unit of claim 1 wherein the housing and the decontamination chamber are (1) hardened to ensure that five exposures to chemical, biological, radiological or nuclear contaminants, decontaminants and decontaminating procedures over a thirty-day period do not cause the housing or decontamination chamber to require corrective maintenance during that thirty-day period; (2) constructed to withstand temperatures ranging from about −32° C. to about 49° C.; (3) constructed to withstand relative humidities ranging from about 5% to about 100%; and (4) constructed to operate when exposed to conventional hazards of solar radiation, rain, fungus, salt fog, sand, dust, vibration and shock.

8. A process for operating the transportable vacuum assisted decontamination unit of claim 1, comprising:
placing one or more contaminated articles in the decontamination chamber;
drawing a vacuum on the decontamination chamber and the contaminated articles therein;
bringing the gaseous decontaminant from the decontaminant processing section into the decontamination chamber;
contacting the contaminated articles in the decontamination chamber with the gaseous decontaminant for a predetermined period of time to decontaminate the contaminated articles;
drawing a vacuum on the decontamination chamber to evacuate residual gaseous decontaminant from the decontamination chamber and to aerate the decontamination chamber and the decontaminated articles contained therein; and
removing the decontaminated articles from the decontamination chamber.

9. The process of claim 8, wherein the decontamination processing section includes a power generator and the process further comprises operating the power generator to provide power to operate the decontaminant generator and the vacuum means.

10. The process of claim 8, wherein the decontaminant comprises a peracid, peroxide, hypochlorite, ozone, or a mixture of two or more thereof.

11. The process of claim 8 wherein the decontaminant comprises hydrogen peroxide.

12. The process of claim 10, wherein the decontaminant further comprises an alkaline gas.

13. The process of claim 8, wherein the decontaminant comprises vaporous hydrogen peroxide and ammonia.

14. The process of claim 13, wherein the evacuated residual gaseous decontaminant comprises hydrogen peroxide, and the process further comprises converting the residual hydrogen peroxide to water vapor and oxygen.

15. The process of claim 8, wherein the contaminated articles comprise one or more of pilot flight equipment, personal protection equipment, military weapons, clothing, body armor, computers, test equipment, optical devices, electronic devices and/or communications equipment.

16. The process of claim 8, wherein the contaminated articles are contaminated with one or more chemical, biological, radiological and/or nuclear warfare agents.

17. The process of claim 8, wherein the contaminated articles are contaminated with one or more bacterial spores, vegetative bacteria, viruses, molds and/or fungi.

18. The process of claim 8, wherein the contaminated articles are contaminated with one or more pathogenic chemical agents.

\* \* \* \* \*